(12) United States Patent
Anastassiades (10) Patent No.: US 7,429,573 B2
(45) Date of Patent: Sep. 30, 2008

(54) METHOD FOR INCREASING THE BONE MINERAL DENSITY AND BONE MICRO-ARCHITECTURE OR CONNECTIVITY OF A MAMMAL USING N-ACYLATED GLUCOSAMINES

(76) Inventor: Tassos Anastassiades, 53 Kensington Avenue, Kingston, Ontario (CA) K7L 4B4

( * ) Notice: Subject to any disclaimer, the term of this patent is extended or adjusted under 35 U.S.C. 154(b) by 547 days.

(21) Appl. No.: 11/211,631

(22) Filed: Aug. 26, 2005

(65) Prior Publication Data
US 2006/0046976 A1 Mar. 2, 2006

(30) Foreign Application Priority Data
Aug. 31, 2004 (CA) .................................. 2479632

(51) Int. Cl.
*A01N 43/04* (2006.01)
*A61K 31/70* (2006.01)
*A61P 3/14* (2006.01)

(52) U.S. Cl. ......................................... 514/62; 536/55.2
(58) Field of Classification Search ....................... None
See application file for complete search history.

(56) References Cited

U.S. PATENT DOCUMENTS

| 3,697,652 A | 10/1972 | Rovati et al. |
| 4,710,491 A | 12/1987 | Lockhoff et al. |

FOREIGN PATENT DOCUMENTS

| DE | 2226273 A * | 12/1982 |
| WO | WO 02/17890 | 3/2002 |

OTHER PUBLICATIONS

Fujita et al., "The effect of active absorbable algal calcium (AAA Ca) with collagen and other matrix components on back and joint pain and skin impedance", *J. Bone Miner Metab*, 2002, 20:298-302, Springer-Verlag.

d'Avis et al, "Age-related changes in effects of insulin-like growth factor I on human osteoblast-like cells", *J. Biochem*, 1997, 324:753-760, Great Britain.

Mobasherl et al., "Glucose transport and metabolism in chondrocytes: a key to understanding chondrogenesis, skeletal development and cartilage degradation in osteoarthritis", *Histol Histopathol*, 2002, 17:1239-1267, UK.

* cited by examiner

*Primary Examiner*—Cecilia Tsang
*Assistant Examiner*—Scarlett Goon
(74) *Attorney, Agent, or Firm*—Jeffrey S. Melcher; Manelli Denison & Selter, PLLC (57) ABSTRACT

A method of treating a mammal for a purpose selected from the group consisting of (a) increasing bone mineral density (BMD), (b) treating low BMD, (c) preventing and treatment of low impact fractures, (d) treatment of high impact fractures; (e) treating osteoporosis; (f) modulating a growth factor that influences bone metabolism; and (g) improving bone micro-architecture or connectivity of bone; the method comprising administering to the mammal an effective amount of a N-acylated-2-glucosamine derivative of the general formula (I):

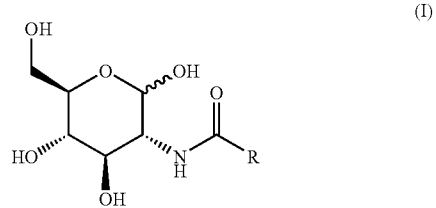

(I)

wherein R is an alkyl radical of the general formula $C_nH_{2n+1}$ and n is selected from 2-12; or pharmaceutically-acceptable salts, esters and glucosides thereof; or pharmaceutically-acceptable compositions thereof.

7 Claims, 5 Drawing Sheets

METHOD FOR INCREASING THE BONE MINERAL DENSITY AND BONE MICRO-ARCHITECTURE OR CONNECTIVITY OF A MAMMAL USING N-ACYLATED GLUCOSAMINES

FIELD OF INVENTION

This invention relates to methods for (a) increasing bone mineral density BMD, (b) treating low (BMD), (c) preventing and treatment of low impact fractures, (d) treatment of high impact fractures, (e) treating osteoporosis, (f) modulating a growth factor that influences bone metabolism; and (g) improving bone micro-architecture or connectivity of a mammal with N-acylated glucosamines, particularly N-butyryl-D-glucosamine.

BACKGROUND TO THE INVENTION

The World Health Organization defines the presence of osteoporosis in humans in terms of low bone mineral density BMD. Individuals whose BMD is less than 2.5 standard deviations below the mean of young normals of their sex in respect of peak bone mass, are considered to have osteoporosis. Individuals whose BMD is less than 1.0 standard deviations below peak bone mass of their sex, are considered to have osteopenia. Osteoporosis results in a higher probability of fracturing bones. It is well known that women have a higher prevalence of osteoporosis and fractures compared to males, and that there is an increased prevalence of osteoporosis and associated increased incidence of fractures after the menopause. Low impact injuries can result in osteoporotic fractures, or so called "fragility fractures". BMD is a good predictor of the probability of developing an osteoporotic fracture, but it is generally agreed that the information that BMD provides is incomplete, as it does examine the quality of bone. BMD is usually measured by a standard radiographic technique, dual energy X-ray absorptiometry (DXA). This is the most standardized technique currently used and has become much more readily available in the Western world for human studies. However, in most of the world DXA is not readily available or is too expensive for routine use. There are many other ways that the presence of osteoporosis can be detected or suspected in humans and other mammals. DXA technology, with suitably adapted software, can be used to reliably assess BMD in animal studies.

Fractures can occur also after high impact, as a result of significant trauma, in individuals with normal bones or osteoporotic or osteopenic bones. The healing of high impact fractures depends on stimulation of new bone formation. Local osteoporosis can occur as a result of immobilization during the treatment of the fracture.

Although BMD is a reasonably good predictor of the risk of fracture in sites such as the hip or spine it is becoming increasingly recognized that there are a number of limitations to the usefulness of BMD measurements. One of the reasons is that DXA technology does not assess bone quality, which depends to a large extent on the micro-architecture of bone. Most drugs used in osteoporosis, such as the bi-phosphonates, increase BMD but do not improve the micro-architecture or the connectivity of bone. Parathyroid hormone administration results in an improvement of trabecular architecture. Glucosamine-based synthetic compounds are not known to improve BMD or bone microarchitecture.

SUMMARY OF THE INVENTION

An object of the present invention is to increase BMD in mammals as a method of preventing the development of osteoporosis.

It is a further object of the invention to provide a method for the treatment of mammals that have low BMD.

It is a still further object of the invention to prevent or diminish the risk of fractures in mammals, as a result of low impact injuries and to enhance healing in fractures that have occurred.

Accordingly, in one broad aspect, the invention provides a method of treating a mammal for a purpose selected from the group consisting of (a) increasing bone mineral density (BMD), (b) treating low BMD, (c) preventing and treatment of low impact fractures,

(d) treatment of high impact fractures;

(e) treating osteoporosis;

(f) modulating a growth factor that influences bone metabolism; and (g) improving bone micro-architecture or connectivity;

said method comprising administering to said mammal an effective amount of a N-acylated-2-glucosamine derivative of the general formula (I):-

(I)

wherein R is an alkyl radical of the general formula $C_nH_{2n+1}$ and n is selected from 2-12; or pharmaceutically-acceptable salts, esters and glucosides thereof; or pharmaceutically-acceptable compositions thereof.

The invention further provides in one aspect a method of increasing the BMD of a mammal said method comprising administering to said mammal an effective amount of an N-acylated-2-glucosamine derivative of the general formula (I), wherein R is an alkyl radical of the general formula $C_nH_{2n+1}$ wherein n is selected from 2-12, or pharmaceutically-acceptable salts, esters and glucosides thereof, or pharmaceutically acceptable compositions, thereof:-

(I)

In preferred embodiments, the invention provides methods as hereinabove defined wherein said N-acylated 2-glucosamine is N-butyryl-D-glucosamine, of the formula II:

(II)

The methods according to the invention can be applied to the treatment of osteoporosis, no matter what method is used for determining the presence of this condition. Also, the invention, can be used as part of the therapy in the treatment of bone fractures.

The anomeric and generic structures of formulas (I) and (II), the physical characteristics of the corresponding compounds, the method for their synthesis and tests for purity are described in U.S. Pat. No. 6,479,469 B2, issued Nov. 12, 2002 to Anastassiades, Tassos.

The N-acylated 2-glucosamines of the general formula (I) may be administered to an animal in an effective, therapeutic amount, for example, by one of the following methods, namely, orally, intravenously, subcutaneously, intramuscularly, trans-dermally, intra-arterially or intra-osseous. The derivatives may be mixed with the food or feed to be ingested by the mammal, or may be administered in a suitable vehicle, in which the active ingredient is either dissolved or suspended. Solution compositions may be water, salt solutions, other solvents, either alone or in combination with compatible nutrients, antibiotics, drugs suited to the condition, including the medical condition of the mammal.

It will be understood by a person skilled in the art that the active N-acylated glucosamines, as hereinbefore defined, should be present and administered in respective, effective and sufficient amounts to prevent or improve low BMD in a mammal. Such a mammal may be in a normal state of health or, otherwise, may be suffering from acute or chronic diseases. The diseases may result in decreased physical activity and treatment medications administered to the said mammal. Decreased physical activity or immobilization or the administration of certain medications may result in or exacerbate low BMD, worsen the micro-architecture and connectivity of bone and, thus, make it more likely that one or more low impact fractures may result.

Thus, synthetically prepared N-acylated glucosamines, as herein-defined, administered to mammals, according to the invention, increase the bone mineral density of said mammal. The term "mammal" in this specification, particularly, includes humans. As a result, the administration of said synthetic N-acylated glucosamines is, thus, also, useful in the prevention and the treatment of osteoporosis and fractures in mammals.

Thus, in a further aspect, the invention provides a method for treating low BMD of a mammal, said method comprising administering to said mammal an effective amount of a compound of the general formula (I), as hereinabove defined.

In a further aspect, the invention provides a method for treating osteoporosis of a mammal, said method comprising administering to said mammal an effective amount of a compound of the general formula (I), as hereinabove defined.

In a further aspect, the invention provides a method for preventing low impact fractures of a mammal, said method comprising administering to said mammal an effective amount of a compound of the general formula (I), as hereinabove defined.

In a further aspect, the invention provides a method for the treatment of low impact fractures of a mammal, said method comprising administering to said mammal an effective amount of a compound of the general formula (I), as hereinabove defined.

In a yet further aspect, the invention provides a method for the treatment of high impact fractures to improve healing of fractures of a mammal, said method comprising administering to said mammal an effective amount of a compound of the general formula (I), as hereinabove defined.

Thus, the invention provides methods of modulating growth factors that influence bone metabolism, such as IGF-1, by the administration of GlcNBu to normal and to an osteopenic or osteoporotic mammal, increasing BMD, improve bone micro-architecture or connectivity, reduction in the risk of fractures and acceleration in the healing of fragility or traumatic fractures, in a mammal where there is an inflammatory condition, such as an arthritis, or other concomitant condition which accelerates the osteopenia or osteoporosis of the mammal and improving bone micro-architecture and connectivity in a mammal with low bone density or osteoporosis and reduction in the risk of fractures and acceleration in the healing of fragility and traumatic fractures.

Thus, in a yet further aspect, the invention provides a method as hereinabove defined for the purpose of modulating a growth factor that influences bone metabolism.

Thus, in a yet further aspect, the invention provides a method as hereinabove defined wherein the growth factor is IGF-1.

Thus, in a yet further aspect, the invention provides a method for the purpose of improving bone micro-architecture and connectivity.

The mammal may be normal or be osteopenic or osteoporotic.

In a yet further aspect, the invention provides a method as hereinabove defined wherein the mammal has an inflammatory condition which is enhancing an osteopenic or osteoporosis condition in the mammal.

In yet a further aspect, the invention provides a method as wherein the inflammatory condition is arthritis.

In a further aspect the invention provides a method as hereinabove defined wherein said effective amount of said N-acylated 2-glucosamine is administered to said mammal in a manner selected from the administrative routes consisting of oral, through the subcutaneous, trans-dermal, intramuscular, intravenous, and intra-osseous administration. In a further aspect the invention provides use of a composition comprising an effective amount of a N-acylated-2-glucosamine derivative of the general formula (I) as hereinabove defined or pharmaceutically-acceptable salts, esters and glucosides thereof; or pharmaceutically-acceptable compositions thereof; and a physiologically acceptable diluent or carrier therefor, for a treatment selected from the group consisting of
(a) increasing bone mineral density (BMD),
(b) treating low BMD,
(c) preventing and treatment of low impact fractures,
(d) treatment of high impact fractures;
(e) treating osteoporosis;
(f) modulating a growth factor that influences bone metabolism; and
(g) improving bone micro-architecture or connectivity of the bones in a mammal.

In a further aspect the invention provides a method of manufacturing a medicament intended for a therapeutic application selected from the group consisting of
(a) increasing bone mineral density (BMD),
(b) treating low BMD,
(c) preventing and treatment of low impact fractures,
(d) treatment of high impact fractures;
(e) treating osteoporosis of a mammal;
(f) modulating a growth factor that influences bone metabolism; and
(g) improving bone micro-architecture or connectivity of the bones of a mammal.

in a mammal characterized in that said method comprising admixing a N-acylated-2-glucosamine derivative of the general formula (I) as hereinabove defined or pharmaceutically-acceptable salts, esters and glucosides thereof; or pharmaceutically-acceptable compositions thereof; and a physiologically acceptable diluent or carrier therefor.

In a further aspect the invention provides use of a pharmaceutical composition for the manufacture of a medicament for the therapeutic application selected from the group consisting of
(a) increasing bone mineral density (BMD),
(b) treating low BMD,
(c) preventing and treatment of low impact fractures,
(d) treatment of high impact fractures;
(e) treating osteoporosis of a mammal;
(f) modulating a growth factor that influences bone metabolism; and
(g) improving bone micro-architecture or connectivity of the bones in a mammal, characterized in that said pharmaceutical composition comprises a N-acylated-2-glucosamine derivative of the general formula (I) as hereinabove defined or pharmaceutically-acceptable salts, esters and glucosides thereof; or pharmaceutically-acceptable compositions thereof; and a physiologically acceptable diluent or carrier therefor.

Preferably, the N-acylated 2-glucosamine in the aforesaid methods and uses according to the invention is N-butyryl-D-glucosamine (II).

BRIEF DESCRIPTION OF THE DRAWINGS AND TABLES

In order that the invention may be better understood, preferred embodiments will now be described, by way of example only, with reference to the accompanying drawings, wherein.

DETAILED DESCRIPTION OF PREFERRED EMBODIMENTS

Example 1

This investigation was designed to test the effects of GlcNBu on the BMD of the femurs in an ovariectomised rat model. The experiments performed are described as follows.

Figure 1A:
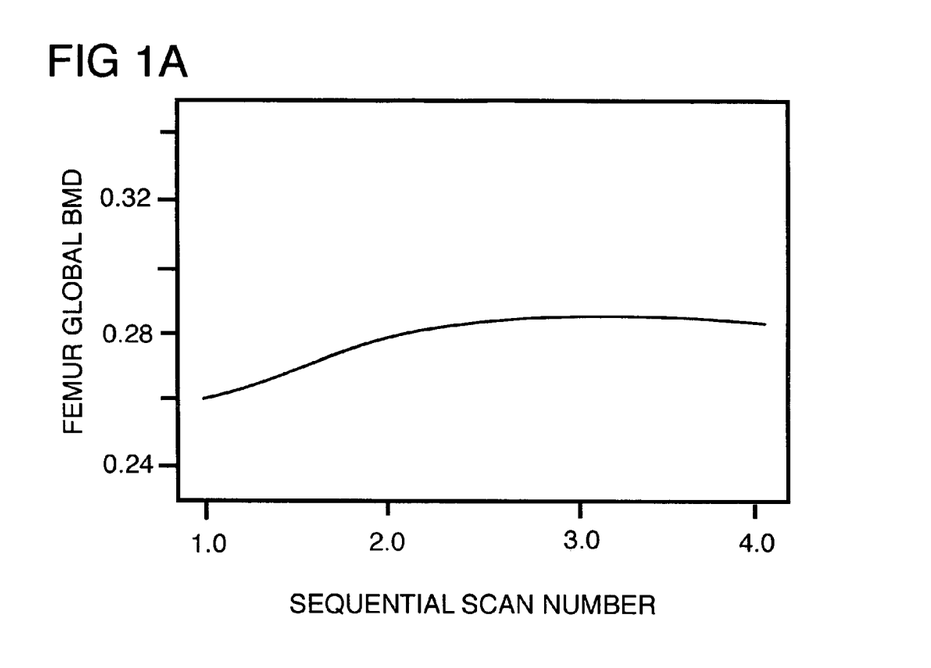
FIGS. 1A and 1B show the BMD for the femurs of control and GlcNBu treated ovariectomised rats relating to Example 1, respectively.
Figure 1B:
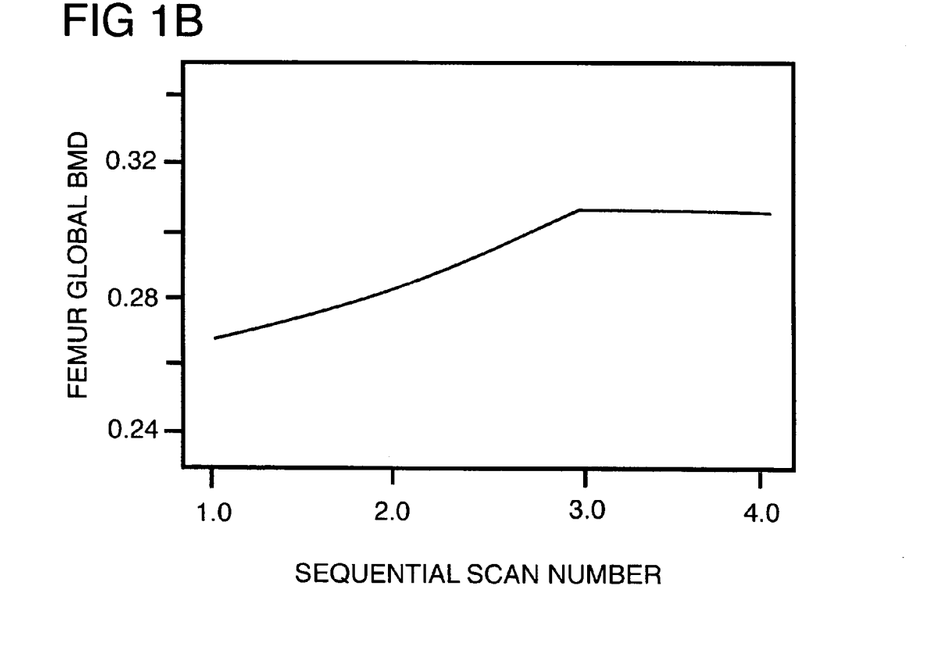

FIGS. 1A and 1B show the effect of GlcNBu feeding on femoral BMD with time, over six months, in the ovariectomized rat. Both the top and bottom panels show the mean total designated herein as global BMD of the femurs for the 8 animals in each group, with time. The actual BMD values are shown on the vertical axes. FIG. 1A Glc-O represents the data from the ovariectomised rats fed with glucose and FIG. 1B GlcNBu-O represents data from the ovariectomised rats fed with GlcNBu. The sequential DXA scans for estimating BMD at times 0, 2 months, 4 months and 6 months are illustrated on the horizontal axis and designated as Sequential Scan number 1.0, 2.0. 3.0 and 4.0, respectively.

Sixteen ovariectomised rats (Charles River Laboratories), approximately 200 g in weight, were randomized into two groups. The control group received 200 mg of glucose, by mouth as single daily doses and the GlcNBu-treated group received 200 mg of GlcNBu by mouth, as single daily doses, for a total period of six (6) months. A similar group of non-ovariectomised animals was fed with GlcNBu or glucose at the same doses. The feeding of the compounds was done in small amounts of peanut butter which was very acceptable to the rats, which were allowed free access to water and rat chow. The animals had the BMDs of the femurs (total or global BMD) and the lumbar spines were estimated at baseline and then at, approximately 2, 4 and 6 months. Consistent position of the femurs was assured with a pre-determined grid. A Hologic 4500 DXA machine, with small animal software, was employed for the study. The animals were lightly anesthetized for each measurement.

At the end of the experiment, the animals were sacrificed, plasma was collected by cardiac puncture, and the femurs removed, fully dissected from adherent tissue and the wet weight was determined. The concentrations of Insulin-like Growth factor 1 (IGF-1) in the plasma, obtained at the end of the experiment, were determined by a commercial immunological method.

As expected, ovariectomised rats demonstrated a decreased BMD in the spine and the hip compared to non-ovariectomised animals, first noted by the DXA measurements at month two. The Figures illustrate that mean BMDs for the ovariectomised groups. In the ovariectomised glucose fed group (control, upper panel) there was a slight increase in femoral BMD up to two months (due to growth of the animals) and then a flattening followed by a slight decline of the BMD. By contrast, the ovariectomised GlcNBu fed animals showed a steady increase in their BMDs until 4 months and then reached a plateau, which was significantly higher ($p<0.05$) than the control (glucose-fed) rats.

The BMDs of the spines showed similar trends as for the femurs, the i.e. largest increases were in the ovariectomised group in the GlcNBu-fed animals of that group, but the differences were not reach statistical significance (data not sown). Also, the non-ovariectomised animals that were fed GlcNBu showed higher trends in the BMD, at the sites measured, compared to the glucose-fed animals but the results were not statistically significant (data not shown).

Figure 2:
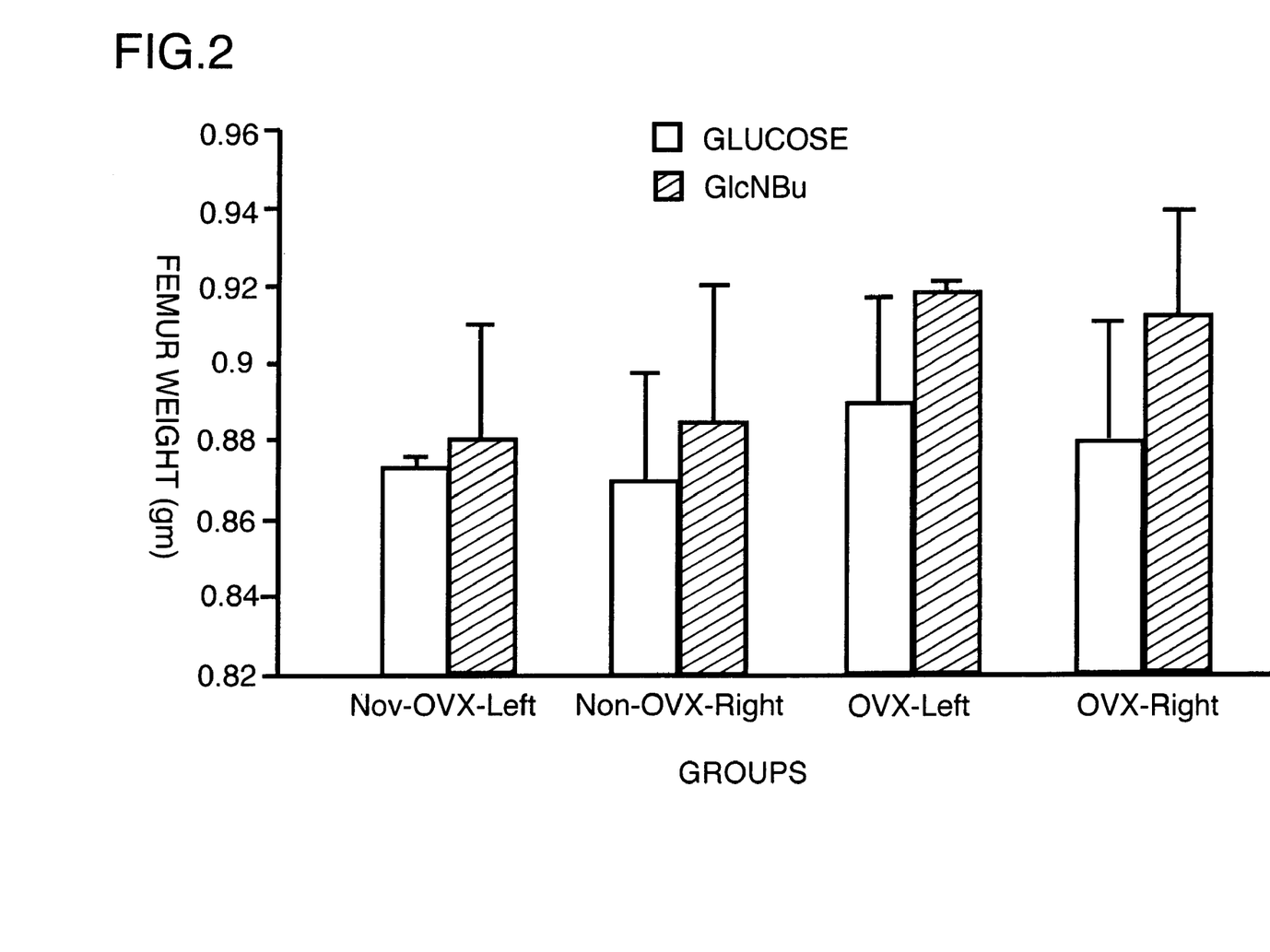
FIGS. 2-6 and Tables 1-3 relate to Example 2, and extend the results for GlcNBu treatments to an arthritis induction model.

FIG. 2 (Example 1) represents wet weight of femurs from ovariectomised and non-ovariectomised animals treated and not-treated with GlcNBu. The results show that oral feeding both non-ovariectomised and ovariectomised animals with GlcNBu increases femoral wet weight, but the effect is greater in the ovariectomised animals.

Figure 3:
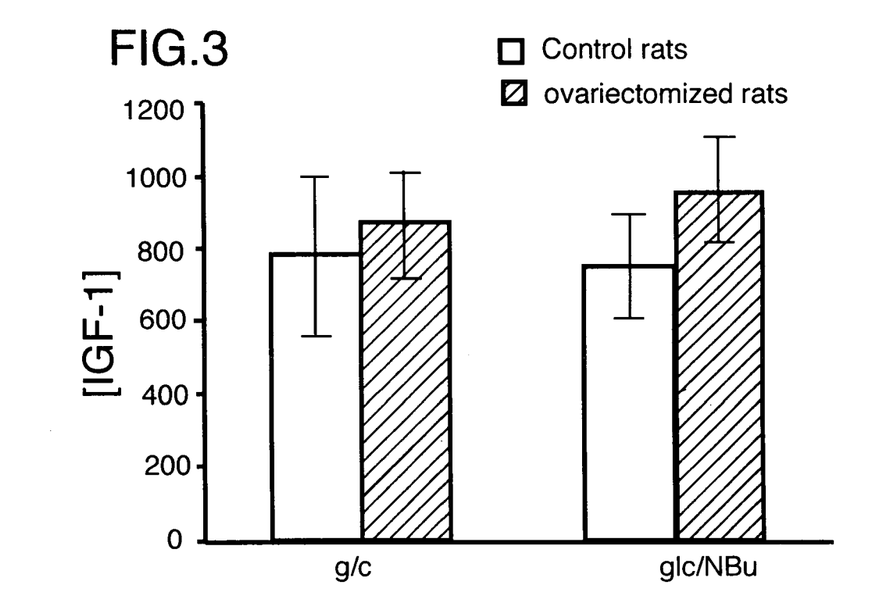

FIG. 3 (Example 1) represents IGF-1 serum levels in ovariectomised GlcNBu-fed rats compared to GlcNBu non-ovariectomised rats. The results show the plasma IGF-1 levels at the end of 6 months in the four groups of animals described in Example 1. There was a significant difference in the concentration of IGF-1 in ovariectomised GlcNBu fed rats compared to GlcNBu fed non-ovariectomised rats ($p=0.044$)

It is concluded that daily feeding of GlcNBu results in increased BMD and wet weight of the femurs of ovariectomised rats, as compared to control animals.

Example 2

In this experiment performed and described herein, there were four groups of Lewis type rats, consisting of eight (8) animals in each group. Lewis type rats had experimental arthritis induced by a single intra-peritoneal injection of streptococcal cell wall antigen (SCW). This type of arthritis has an acute and chronic phase and affects mostly the distal joints in the hind limbs of the animals, and, less so, the knees and hips. Groups 1-3, inclusive, had inflammatory arthritis induced. The compound used in the experiment was used to supplement normal rat chow feed on a daily basis. Feed and water were unrestricted.

Group 1 feed was supplemented with the compound shown in formula II, abbreviated as GlcNBu, at a dose of 200 mg/kg/day.

Group 2 feed was supplemented with glucose, abbreviated as Glc, at 200 mg/kg/day (control group).

Group 3 feed was supplemented with GlcNBu at 20 mg/kg/day.

Group 4, was a normal Group, without arthritis.

At the end of 6 weeks, the animals were sacrificed, the femurs and tibias were excised, fixed in formalin and the BMD, micro-CT measurements, 3-dimentional measurements and two-dimentional subchondral bone analysis were carried out, by the methods detailed below.

BMD. All the dissected femurs and tibiae were scanned with dual energy x-ray absorptiometry (DXA) were measured at the distal femur, and proximal tibia using a user defined region of interest (ROI).

Micro-CT imaging protocol. The fixed left tibiae were scanned with micro-CT scanner (Explore Locus SP micro CT Scanner, GE Healthcare). The tibias were placed in a water filled specimen tube in a firmed position such that the main axis was kept as parallel as possible to the Z-axis of the micro-CT image coordinate system. The reconstructed tibia images were analyzed with MicroView 2.0 software (GE Healthcare, London, ON) in two and three dimensions.

Three-dimensional trabecular bone measurements. Three dimensional bone analyses were conducted using three selected ROIs using MicroView 2.0 analysis software. On 3D analysis, the tissue volume (3D-TV, mm3) and trabecular bone volume (3D-BV, mm3) were measured directly, and the fractional trabecular bone volume (3D-BV/TV, %) was calculated. The trabecular thickness (3D-Tb.Th, μm) and trabecular number (3D-Tb.N, N/mm) were measured directly on 3D images. Another parameter obtained is the structure model index (SMI). The SMI represented the plate-rod characteristics of trabecular structure. In this measure, a negative number is indicative of a plate-like structure containing holes, 0 represents an ideal plate-like structure while 3 represents the ideal rod (cylindrical) structure. Larger SMI values indicate that trabecular structure contains a more rod-like structure in older or diseased bone.

Three-dimensional isosurface. A 3-D isosurface image of each tibia was obtained by a volume-rendering function in MicroView to qualitatively examine the erosive damage in the bone surface.

Two-dimensional subchondral bone analysis. Three coronal sections of proximal tibia were obtained from each 3-D reconstructed tibia image: anterior, central, and posterior (1 mm apart). The subchondral trabecular bone structure and connectivity in the epiphyseal region of the proximal tibia was analyzed using an image processing and analysis system (Quantimet 570, Leica) on the 2-D micro-CT images. Fractional trabecular bone volume (2D-BV/TV, %), trabecular thickness (2D-Tb.Th) and trabecular number (2D-Tb.N, N/mm).

The connectivity parameters obtained in the analysis include: Number of multiple points (1/mm2), Number of end points (1/mm2), Lengths of node- node struts (mm/mm2), Lengths of free-free struts (mm/mm2), and Total strut length (mm/mm2).

The subchondral bone plate thickness (Sb.Pl.Th, mm) was also measured on the central section of the 2D micro-CT proximal tibia images using individual point-to-point distance measures. The thickness was calculated by averaging 12 measurements per tibia. All measurements were made in a standardized viewing area by a single observer who was blinded to the experiment.

Statistical Analysis. One-way analysis of variance (ANOVA) with Fisher's least significant difference (LSD) post-hoc test was used to compare means. Significance was considered at $p<0.05$ and presented as mean±standard error of the mean (SEM).

In FIGS. 4-7, the BMD data are shown as bar graphs and the values can be read on the vertical axis. The Experimental Group (1-4) are indicated on the horizontal axis. The means and standard deviations of the BMDs are shown for each bar graph as linear T-bars.

Figure 4:
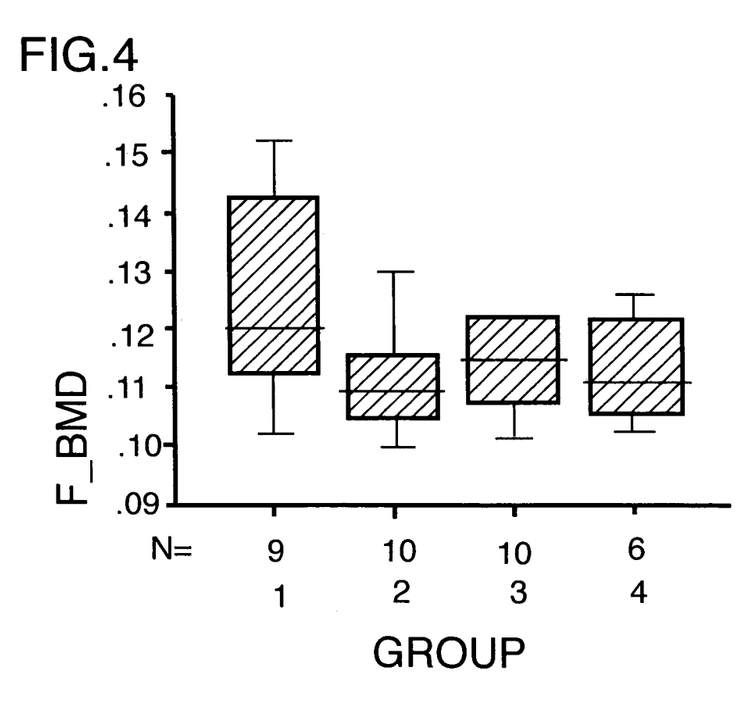
Figure 5:
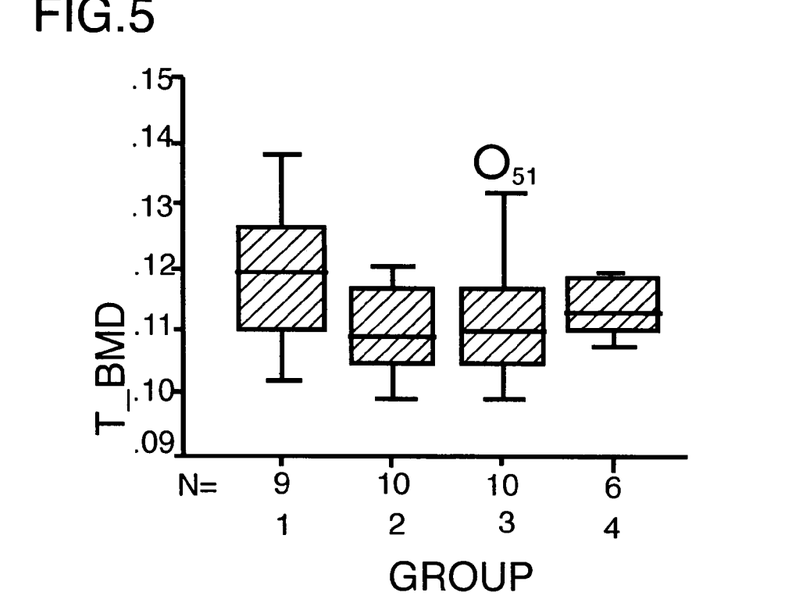

FIG. 4 and FIG. 5 show the total BMD for the whole left femur and left tibia in the Experimental Groups, respectively. The right femur and tibia showed similar results to the left side.

BMD were also determined in so-called "Regions of Interest" (ROI), which were pre-defined as identical geometrical regions in the sub-chondral bone of the femurs and tibias, respectively.

Figure 6:
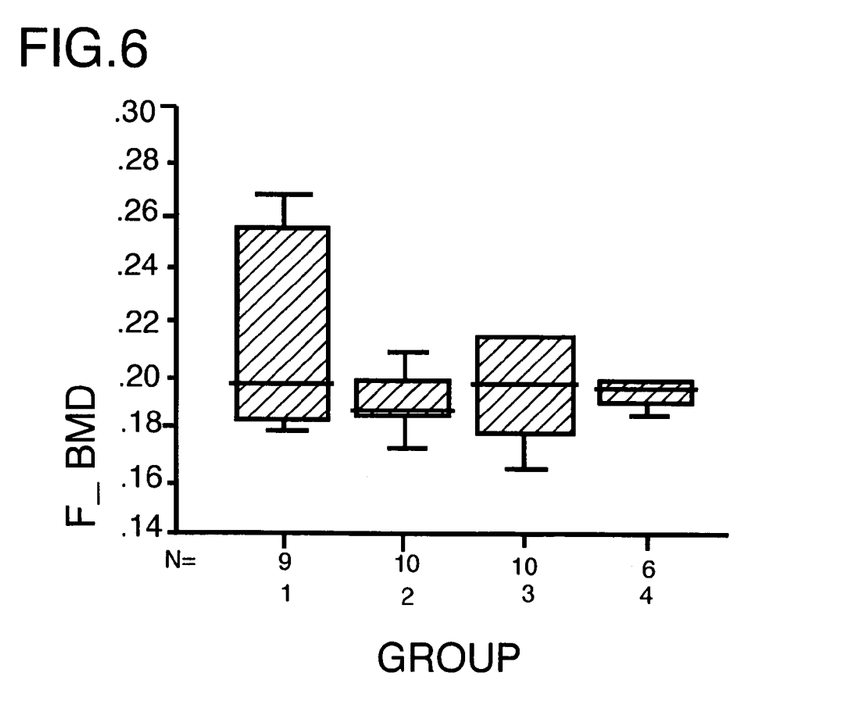
Figure 7:
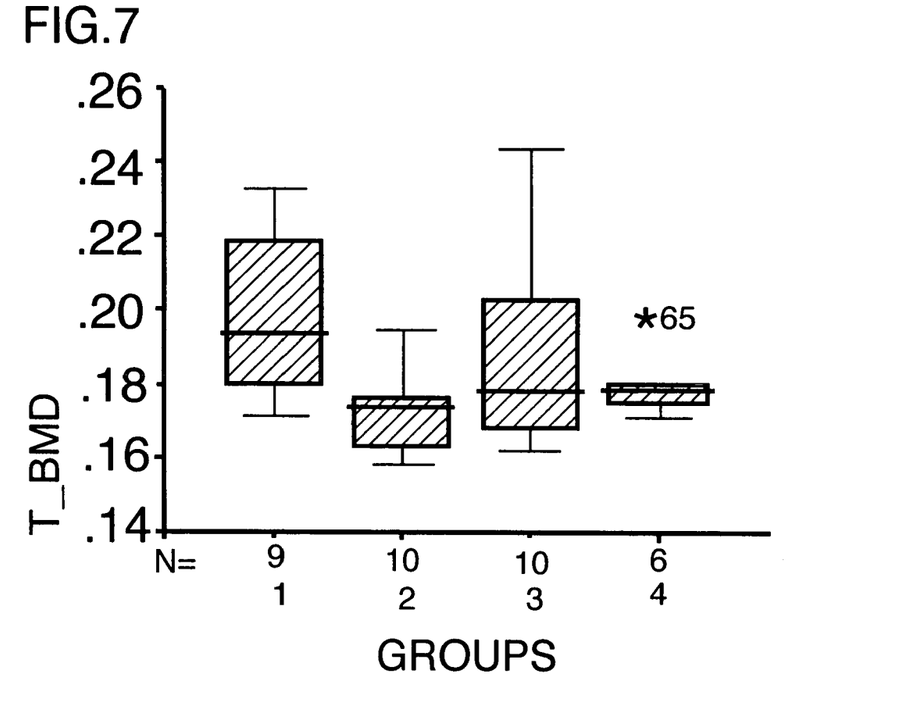
FIG. 7 shows the BMD for the ROI for the left tibia.

FIG. 6 and FIG. 7 show the BMD for the ROI for the left femur and tibia, respectively. The ROI data for the right femur and tibia were similar to the left side.

Figure 8:
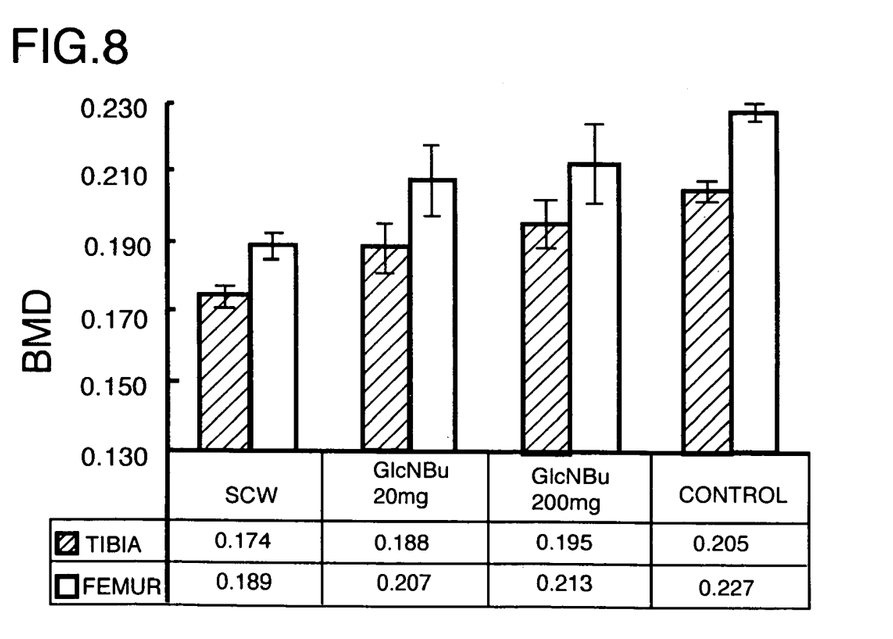
FIG. 8 shows overall DXA values for the BMD in femurs and tibias for SCW-arthritis rats.

The overall results for the BMD from Example 2 are summarized in FIG. 8 wherein the overall averages are indicated for the BMDs in both femurs and tibia for the SCW-arthritis rats (designated SCW) and the SCW-arthritis rats treated with the lower (20 mg) and higher (200 mg) concentrations of GlcNBu (designated GlcNBu 20 mg and GlcNBu 200 mg, respectively.

It can be seen that in Group 1 (GlcNBu 200 mg) BMD were much greater than Group 3 (GlcNBu 20 mg). Group 2 BMDs were somewhat greater than Group 4 (No arthritis/untreated). Group 4 BMDs were similar to Group 2(Glucose 200 mg). Statistical significance of the differences was achieved between Group 1 and other Groups, as shown.

In general, trabecular bone volume, trabecular number and thickness were significantly decreased in the joints involved with arthritis compared to the controls. Similar changes was observed in both 2D and 3D images. These changes were corrected by GlcNBu treatment in a dose dependent manner, so that high dose GlcNBu treatment was similar to the controls. The metaphyseal region demonstrated a less marked increase in trabecular volume between low and high dose groups; however there was a significant increase of 12% from Group2 to the GlcNBu treated groups (p <0.05). The metaphyseal bone structure changes suggest that GlcNBu functions systemically.

Specific findings are outlined below.

Subchondral Plate Thickness was decreased in the RA group, and this change was minimized by GlcNBu treatment, especially in the high dose treatment group. Table 1 presents the mean trabecular volume, trabecular number, trabecular thickness, and subchondral plate thickness data for each of the SCW-arthritis induced groups (indicated in Table 1 by RA) in the epiphyseal and metaphyseal regions. Each of these parameters increased with the dose of GlcNBu. There were more significant bone changes occurred in the high dose group. The metaphysis was significantly affected in both the high and low dose groups.

TABLE 1

Mean values for trabecular bone volume (%), trabecular number, trabecular thickness (mm) and subchondral plate thickness (mm)

| Treatment | Region of proximal tibia | Trabecular Bone Volume (%) | Trabecular Number | Trabecular Thickness (mm) | Subchondral Plate Thickness (mm) |
|---|---|---|---|---|---|
| SCW + GlcNBu High | lateral epiphysis | 36.9 ± 3.7 | 6.0 ± 0.6 | 0.054 ± 0.008 | 0.11 ± 0.04 |
| | medial epiphysis | 36.3 ± 4.8 | 5.1 ± 0.7 | 0.066 ± 0.014 | 0.07 ± 0.04 |
| | metaphysis | 32.6 ± 4.7 | 8.2 ± 1.5 | 0.034 ± 0.004 | |
| SCW | lateral epiphysis | 32.6 ± 3.0 | 5.5 ± 0.4 | 0.050 ± 0.004 | 0.07 ± 0.01 |
| | medial epiphysis | 32.7 ± 4.2 | 4.8 ± 0.5 | 0.060 ± 0.007 | 0.07 ± 0.03 |
| | metaphysis | 22.5 ± 7.4 | 6.8 ± 1.8 | 0.027 ± 0.003 | |
| SCW + GlcNBu Low | lateral epiphysis | 33.7 ± 2.7 | 5.8 ± 0.5 | 0.052 ± 0.008 | 0.10 ± 0.04 |
| | medial epiphysis | 33.1 ± 3.0 | 5.0 ± 0.4 | 0.062 ± 0.011 | 0.07 ± 0.03 |
| | metaphysis | 34.4 ± 9.4 | 7.7 ± 1.3 | 0.034 ± 0.005 | |

Cancellous bone connectivity. Strut analysis showed a significant increase ($p=0.034$) in the length of node-to-node struts from the untreated arthritis-induced group to the high dose group on the medial side of the proximal epiphysis. The connectivity parameters are presented in Table 2. The results indicate a dose-dependent increase in bone connectivity. Designations are as for Table 1.

TABLE 2

Comparison of bone changes in the proximal tibia resulting from high and low dosages of GlcNBu

| Dosage group compared | Region of proximal tibia | Trabecular Bone Volume (%) | Structure Model Index | Trabecular Separation | Trabecular Number | Trabecular Thickness (mm) | Subchondral Plate Thickness (mm) |
|---|---|---|---|---|---|---|---|
| GlcNBu High Dose vs SCW | lateral epiphysis | ↑↑ | ↓ | ↓↓ | ↑↑ | ↑ | ↑↑ |
| | medial epiphysis | ↑ | ↓ | ↓ | ↑ | ↑ | ↑ |
| | metaphysis | ↑↑ | ↓↓ | ↓↓ | ↑↑ | ↑↑ | |
| GlcNBu Low Dose vs SCW | lateral epiphysis | ↑ | ↓ | ↓↓ | ↑ | ↑ | ↑ |
| | medial epiphysis | ↑ | ↓ | ↓↓ | ↑ | ↑ | ↑ |
| | metaphysis | ↑↑ | ↓↓ | ↓ | ↑ | ↑↑ | |

The arrows indicate a bone change when compared to untreated RA-induced rats. Changes are considered significant when p values < 0.05.
↑↑: significant increase
↑: increase
↓↓: significant decrease
↓: decrease Site-specific structure change. Regional differences were observed in both 2D and 3D analysis. In 3D analysis, the metaphysis showed significant change over the epiphysis region. Comparing the 2D analysis among the three sections, the posterior side presented the highest bone volume, thickness and connectivity. Moreover, the higher bone mass and more connected cancellous bone is more apparent in the medial side rather than the lateral side, but the lateral region exhibits more significant disease change and appears to have responded to the treatment more than the medial side. These changes suggest that more weight bearing related to higher bone mass and connectivity (probably stronger as well) and less affected by disease. However, the anterior section was the most affected site by the disease, there were 45% loss in bone volume 33% loss in Tb.Th., GlcNBu. Comparison of the isosurfaces in the studied groups demonstrate that GlcNBu effectively protects bone from further erosion in this model of chronic inflammatory arthritis.

Structure model index (SMI). The untreated SCW group had significantly higher SMI values ($p<0.05$) in both epiphyses and tetaphysic regions compared to the Control, indicating that the arthritic trabecular bones were altered towards a rod-like structure. Whereas the GlcNBu treated groups have 15-33% correction in SMI values compared to the untreated group in the three tested areas. Correspondingly, the trabecular separation was increased in the SCW group and this change was significantly reduced by GlcNBu treatment.

TABLE 3

(Example 2) shows the trabecular bone strut analysis and percentage loss in bone parameters.

| | | Regions | | | | | | | | | | | |
|---|---|---|---|---|---|---|---|---|---|---|---|---|---|
| | | Anterior/ lateral | | Anterior/ medial | | Middle section/ lateral | | Middle section/ medial | | Posterior/ lateral | | Posterior/ medial | |
| Parameters | GROUP | Mean ± SEM | % loss | Mean ± SEM | % loss | Mean ± SEM | % loss | Mean ± SEM | % loss | Mean ± SEM | % loss | Mean ± SEM | % loss |
| 2D-BV/TV, % | SCW | 21.8 ± 1.5 | 45 | 24.8 ± 1.6 | 39 | 21.4 ± 1.3 | 25 | 28.7 ± 1.6 | 32 | 27.6 ± 1.4 | 13 | 34.1 ± 1.3 | 25 |
| | SCW + 20 mg | 23.7 ± 2.3 | 40 | 27.2 ± 1.4 | 33 | 24.9 ± 1.6 | 13 | 29.2 ± 2.3 | 31 | 24.9 ± 1.5 | 21 | 36.2 ± 1.6 | 20 |
| | SCW + 200 mg | 24.8 ± 3.4 | 37 | 27.8 ± 2.7 | 31 | 24.1 ± 2.1 | 15 | 35.1 ± 4.1 | 17 | 23.2 ± 1.0 | 27 | 35.9 ± 2.2 | 21 |
| | Control | 39.5 ± 0.3 | 0 | 40.4 ± 0.3 | 0 | 28.5 ± 0.4 | 0 | 42.1 ± 5.2 | 0 | 31.6 ± 0.7 | 0 | 45.3 ± 0.5 | 0 |
| 2D-Tb.Th.um | SCW | 38.2 ± 2.6 | 33 | 45.3 ± 3.0 | 34 | 49.3 ± 1.9 | 20 | 59.6 ± 2.4 | 34 | 53.4 ± 1.8 | 17 | 57.0 ± 1.8 | 26 |
| | SCW + 20 mg | 38.7 ± 1.7 | 32 | 48.6 ± 1.6 | 29 | 54.3 ± 2.8 | 11 | 63.0 ± 4.0 | 30 | 51.8 ± 1.6 | 19 | 59.3 ± 2.3 | 23 |
| | SCW + 200 mg | 39.7 ± 2.9 | 30 | 49.5 ± 4.3 | 28 | 51.3 ± 2.8 | 16 | 68.5 ± 6.3 | 24 | 49.8 ± 1.7 | 22 | 61.0 ± 3.6 | 21 |
| | Control | 56.7 ± 4.3 | 0 | 68.9 ± 3.9 | 0 | 61.3 ± 3.1 | 0 | 90.4 ± 5.8 | 0 | 64.2 ± 7.7 | 0 | 77.2 ± 4.4 | 0 |
| 2D-Tb.N./ mm | SCW | 5.7 ± 0.3 | 23 | 5.6 ± 0.3 | 13 | 4.3 ± 0.2 | 7 | 4.8 ± 0.2 | -4 | 5.2 ± 0.2 | -1 | 6.0 ± 0.2 | 6 |
| | SCW + 20 mg | 5.8 ± 0.4 | 21 | 5.6 ± 0.3 | 12 | 4.6 ± 0.2 | 2 | 4.6 ± 0.2 | 1 | 4.8 ± 0.2 | 7 | 6.2 ± 0.2 | 3 |
| | SCW + 200 mg | 6.0 ± 0.7 | 20 | 5.7 ± 0.6 | 10 | 4.7 ± 0.3 | 0 | 5.1 ± 0.2 | -9 | 4.5 ± 0.2 | 13 | 6.1 ± 0.2 | 5 |
| | Control | 7.4 ± 0.5 | 0 | 6.4 ± 0.6 | 0 | 4.7 ± 0.2 | 0 | 4.6 ± 0.3 | 0 | 5.2 ± 0.5 | 0 | 6.4 ± 0.5 | 0 |
| End Points | SCW | 40.5 ± 5.6 | -161 | 30.0 ± 4.1 | -123 | 21.9 ± 2.6 | -11 | 15.8 ± 2.2 | -217 | 16.3 ± 1.2 | -62 | 20.8 ± 1.9 | -306 |
| | SCW + 20 mg | 36.2 ± 2.5 | -134 | 22.5 ± 1.7 | -67 | 17.5 ± 1.9 | -69 | 14.1 ± 2.3 | -184 | 20.0 ± 1.8 | -100 | 16.2 ± 2.1 | -216 |
| | SCW + 200 mg | 34.1 ± 4.1 | -120 | 26.7 ± 5.7 | -99 | 19.8 ± 1.7 | -92 | 12.2 ± 2.1 | -145 | 21.4 ± 1.7 | -114 | 17.1 ± 1.8 | -233 |
| | Control | 15.5 ± 6.2 | 0 | 13.4 ± 3.8 | 0 | 10.3 ± 2.5 | 0 | 5.0 ± 1.1 | 0 | 10.0 ± 1.3 | 0 | 5.1 ± 1.5 | 0 |
| Multiple points | SCW | 7.5 ± 1.1 | 54 | 8.5 ± 1.2 | 47 | 6.8 ± 1.3 | 31 | 9.0 ± 1.0 | 21 | 9.8 ± 0.7 | 44 | 13.7 ± 0.8 | 30 |
| | SCW + 20 mg | 9.3 ± 1.6 | 43 | 9.2 ± 1.0 | 42 | 8.3 ± 1.1 | 16 | 9.9 ± 1.1 | 13 | 7.8 ± 0.8 | 55 | 12.6 ± 1.4 | 36 |
| | SCW + 200 mg | 10.3 ± 2.7 | 37 | 10.7 ± 1.7 | 32 | 9.5 ± 1.9 | 2 | 12.6 ± 1.8 | -11 | 7.1 ± 0.7 | 59 | 13.9 ± 1.8 | 29 |
| | Control | 16.4 ± 4.5 | 0 | 15.8 ± 1.3 | 0 | 9.8 ± 0.2 | 0 | 11.3 ± 0.3 | 0 | 17.4 ± 2.2 | 0 | 19.7 ± 8.5 | 0 |
| Node-node struts | SCW | 0.7 ± 0.2 | 80 | 0.9 ± 0.2 | 61 | 0.7 ± 0.2 | 29 | 1.2 ± 0.2 | 41 | 1.3 ± 0.2 | -1 | 1.5 ± 0.1 | 46 |
| | SCW + 20 mg | 0.8 ± 0.2 | 75 | 1.2 ± 0.2 | 47 | 1.0 ± 0.2 | 3 | 1.2 ± 0.2 | 42 | 0.9 ± 0.1 | 30 | 1.7 ± 0.3 | 37 |
| | SCW + 200 mg | 1.2 ± 0.4 | 64 | 1.3 ± 0.3 | 45 | 0.9 ± 0.2 | 15 | 2.0 ± 0.3 | 4 | 0.7 ± 0.1 | 46 | 2.1 ± 0.3 | 23 |
| | Control | 3.3 ± 0.4 | 0 | 2.3 ± 0.6 | 0 | 1.0 ± 0.1 | 0 | 2.1 ± 0.0 | 0 | 1.3 ± 0.4 | 0 | 2.7 ± 0.8 | 0 |
| Total Strut length | SCW | 4.9 ± 0.2 | 34 | 4.8 ± 0.2 | 19 | 3.8 ± 0.2 | 17 | 4.3 ± 0.2 | 10 | 4.8 ± 0.2 | -1 | 5.5 ± 0.2 | 14 |
| | SCW + 20 mg | 5.3 ± 0.4 | 30 | 5.1 ± 0.3 | 14 | 4.0 ± 0.2 | 14 | 4.2 ± 0.3 | 11 | 4.3 ± 0.2 | 11 | 5.7 ± 0.3 | 10 |
| | SCW + 200 mg | 5.4 ± 0.7 | 28 | 5.1 ± 0.5 | 15 | 4.2 ± 0.2 | 9 | 4.9 ± 0.3 | -2 | 4.0 ± 0.2 | 16 | 5.6 ± 0.3 | 12 |
| | Control | 7.5 ± 0.9 | 45 | 5.9 ± 0.7 | 39 | 4.6 ± 0.3 | 25 | 4.7 ± 0.3 | 32 | 4.8 ± 0.1 | 13 | 6.3 ± 1.0 | 0 |

34% reduce in total skeleton length, 54% decrease in multiple points and as much as 80% decrease in node-node struts (Table 2).

Joint integrity. Isosurfaces generated from the scan of diseased bone show clear bone erosion at the joint margin. Nevertheless, protection of the bone erosions were observed in the GlcNBu treated group, especially in high dose. Photographs of the isosurfaces of proximal rat tibia in a) No arthritis, no treatment; (b) arthritis, no treatment; (c) arthritis+low dose GlcNBu; (d) arthritis+high dose GlcNBu groups studies have indicated the degrees of preservation of subchondral bone with increasing doses of Although this disclosure has described and illustrated certain preferred embodiments of the invention, it is to be understood that the invention is not restricted to those particular embodiments. Rather, the invention includes all embodiments which are functional or mechanical equivalents of the specific embodiments and features that have been described and illustrated.

I claim:

1. A method of treatment of osteoporosis in a mammal in need thereof, comprising administering to said mammal an effective amount of a N-acylated-2-glucosamine derivative of the general formula (I):

(I)

wherein R is an alkyl radical of the general formula $C_nH_{2n+1}$ and n is selected from 2-12; or pharmaceutically-acceptable salts, esters, and glucosides thereof; or pharmaceutically-acceptable compositions thereof.

2. A method of increasing the bone mineral density (BMD) in a mammal in need thereof, comprising administering to said mammal an effective amount of a N-acylated-2-glucosamine derivative of the general formula (I):

(I)

wherein R is an alkyl radical of the general formula $C_nH_{2n+1}$ and n is selected from 2-12; or pharmaceutically-acceptable salts, esters, and glucosides thereof; or pharmaceutically-acceptable compositions thereof.

3. A method of treatment of low BMD in a mammal in need thereof, comprising administering to said mammal an effective amount of a N-acylated-2-glucosamine derivative of the general formula (I):

(I)

wherein R is an alkyl radical of the general formula $C_nH_{2n+1}$ and n is selected from 2-12; or pharmaceutically-acceptable salts, esters, and glucosides thereof; or pharmaceutically-acceptable compositions thereof.

4. A method of treatment of low impact fractures in a mammal in need thereof, comprising administering to said mammal an effective amount of a N-acylated-2-glucosamine derivative of the general formula (I):

(I)

wherein R is an alkyl radical of the general formula $C_nH_{2n+1}$ and n is selected from 2-12; or pharmaceutically-acceptable salts, esters, and glucosides thereof; or pharmaceutically-acceptable compositions thereof.

5. A method of treatment of high impact fractures in a mammal in need thereof, comprising administering to said mammal an effective amount of a N-acylated-2-glucosamine derivative of the general formula (I):

(I)

wherein R is an alkyl radical of the general formula $C_nH_{2n+1}$ and n is selected from 2-12; or pharmaceutically-acceptable salts, esters, and glucosides thereof; or pharmaceutically-acceptable compositions thereof.

6. A method as defined in any of claims 1-3 or 4-5 wherein said N-acylated-2-glucosamine is N-butyryl-D-glucosamine of the formula (II):

(II)

or pharmaceutically acceptable salts, esters and glucosides thereof; or pharmaceutically-acceptable compositions thereof.

7. A method as defined in any of claims claim 1-3 or 4-5 wherein said effective amount of said N-acylated-2-glucosamine is administered to said mammal in a manner selected from the administrative routes consisting of oral, subcutaneous, trans-dermal, intra-muscular, intravenous, and intra-osseous administration.

* * * * *